United States Patent [19]

Nakatsu et al.

[11] Patent Number: 6,123,945
[45] Date of Patent: Sep. 26, 2000

[54] WATER-SOLUBLE ANTI-OXIDATION AGENTS

[75] Inventors: Tetsuo Nakatsu, Chappaqua, N.Y.; Akiko Yamasaki, New Milford, N.J.

[73] Assignees: Takasago International Corporation, Japan; Takasago Institute for Interdisciplinary Science, Inc., Rockleigh, N.J.

[21] Appl. No.: 09/140,238

[22] Filed: Aug. 26, 1998

[51] Int. Cl.$^7$ ..................................................... A61K 35/78
[52] U.S. Cl. ........................................................... 424/195.1
[58] Field of Search ........................................... 424/195.1

[56] References Cited

U.S. PATENT DOCUMENTS 3,890,433  6/1975  Oishi et al. ................................ 424/37
4,839,187  6/1989  Mai et al. .................................. 426/542

OTHER PUBLICATIONS

Osawa, T., Food Sci., vol. 24(6), 679–689, Dec. 1997.
Chung, K.T. et al., Critical Reviews in Food Science and Nutrition, vol. 38(6), p. 421–464, Aug. 1998.

*Primary Examiner*—Jean C. Witz
*Attorney, Agent, or Firm*—Morrison Law Firm

[57] ABSTRACT

Fat removal processing of herbs, such as those used in food seasoning, is conducted by using carbon dioxide liquid and/or an organic solvent, or carbon dioxide gas at subcritical or supercritical conditions. Hydrated alcohol is added to the residual oil-insoluble portion. Activated carbon is added to the resulting hydrated alcohol-containing extraction solution. After stirring, the activated carbon is removed. From the resulting solution, water and alcohol are removed, and a water soluble anti-oxidation agent is obtained.

2 Claims, 4 Drawing Sheets

WATER-SOLUBLE ANTI-OXIDATION AGENTS

BACKGROUND OF THE INVENTION

The present invention relates to water-soluble anti-oxidation agents and a manufacturing process for the same.

Many substances derived from herbs are known to modulate oxidation of fats, oils and lipids, and are also known to control inflammation of the skin. In particular, many anti-oxidation agents have been extracted and acquired from herbs commonly used as food seasonings. The manufacturing process for these is disclosed in many references and patents, but many of these known anti-oxidation agents are water-insoluble aromatic compounds.

The anti-oxidation agents which are currently in widespread use are principally oil-soluble substances. These include anti-oxidation agents obtained from natural sources, such as tocopherols, and synthesized anti-oxidation agents, such as dibutylhydroxytoluene (BHT) and butylhydroxyanisole (BHA). Except for certain types of manufactured products which have a relatively high water content, such as processed products and beverages, cosmetic products, and toiletry products, these oil-soluble anti-oxidation agents are not suitable due to their lack of solubility in aqueous solutions.

In view of these problems, a water-soluble anti-oxidation agent which can be added to the previously mentioned manufactured products, which is very safe, and which can be obtained inexpensively from natural products is desirable.

Examples of disclosures regarding water-soluble anti-oxidizing agents derived from seasoning herbs include Japanese Examined Patent Number 55-18,435, Japanese Examined Patent Number 57-57,109, and Japanese Examined Patent Number 58-37,351. All of these describe only a process of extracting anti-oxidation components through the use of hydrated alcohol.

In Japanese Laid Open Patent Number 4-53,895, a seasoning herb is processed with carbon dioxide which is in a liquid state, subcritical state, or supercritical state. After the odor component of the herb is extracted and removed, the anti-oxidation agent is obtained by precipitation from water. However, the anti-oxidizing agent obtained with this process is not water-soluble.

OBJECTS AND SUMMARY OF THE INVENTION

It is an object of the present invention to overcome the limitations of the prior art.

It is another object of the present invention to provide a water-soluble anti-oxidation agent having superior anti-oxidation and/or anti-inflammatory properties.

Briefly stated, fat removal processing of herbs, such as those used in food seasoning, is conducted by using carbon dioxide liquid, and/or an organic solvent, or carbon dioxide gas at subcritical or critical conditions. Hydrated alcohol is added to the residual oil-insoluble portion. Activated carbon is added to the resulting hydrated alcohol-containing extraction solution. After stirring, the activated carbon is removed. From the resulting solution, water and alcohol are removed, and a water-soluble anti-oxidation agent is obtained.

According to an embodiment of the present invention, a method for producing a water-soluble anti-oxidation agent comprises the steps of processing food seasoning herbs to remove fats and oils using liquid carbon dioxide, such that an oil-insoluble residue portion is produced, contacting the oil-insoluble residue portion with hydrated alcohol to produce a mixture, and removing water and alcohol from the mixture, whereby the water-soluble anti-oxidation agent is produced.

According to another embodiment of the present invention, a water-soluble anti-oxidation agent is produced by using a solvent mixture, such that an oil-insoluble residue portion is produced, contacting the oil-insoluble residue portion with hydrated alcohol to produce a mixture, and removing water and alcohol from the mixture, whereby the water-soluble anti-oxidation agent is produced.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
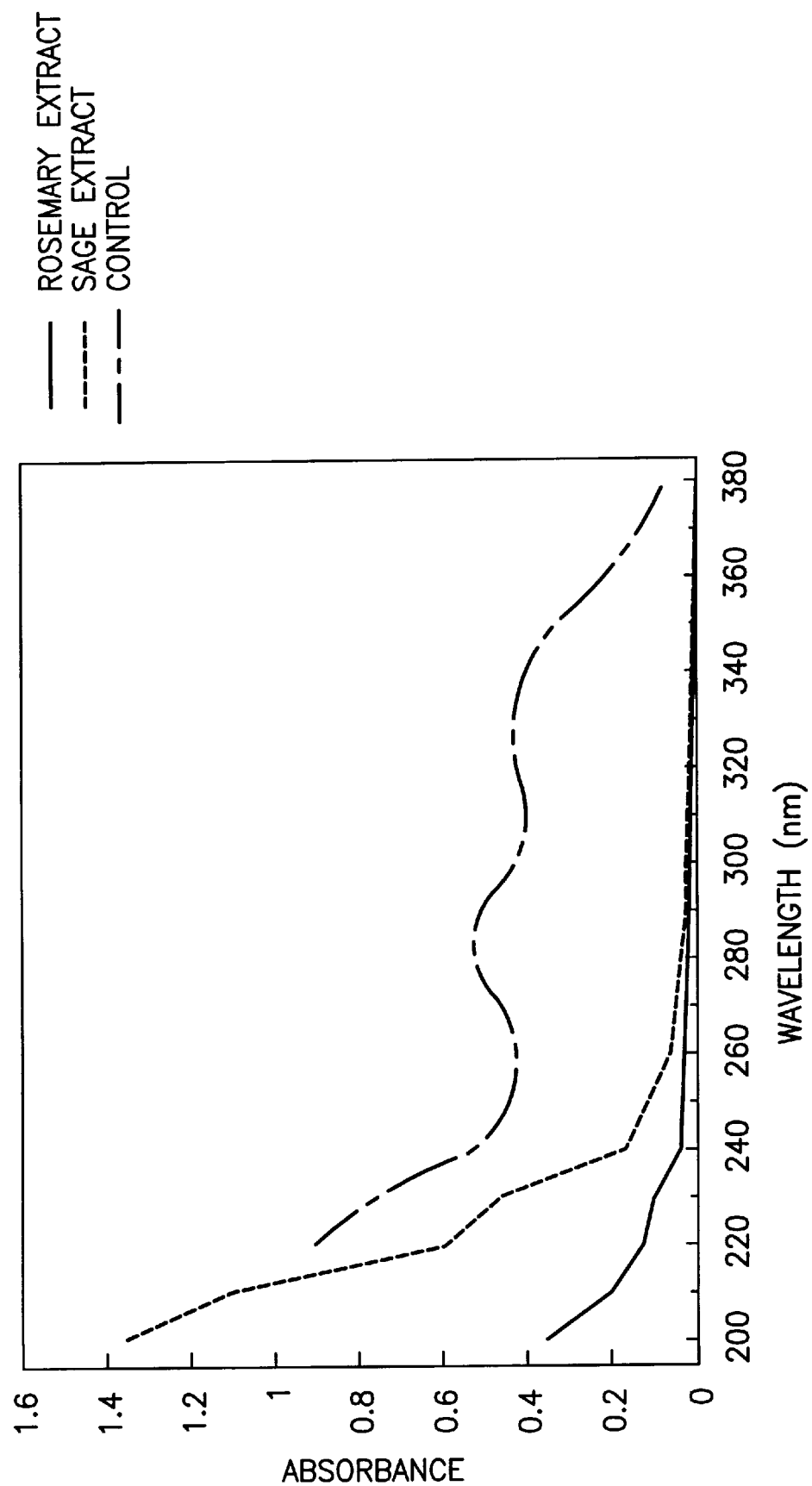
FIG. 1 is a graph showing the ultraviolet absorption spectra of the compounds of the present invention.

In the method of the present invention, seasoning herbs are directly processed to remove fats and oils by using liquid carbon dioxide gas and/or organic solvents. Hydrated alcohol is added to the residual oil-insoluble portion. Activated carbon may then be added to the hydrated alcohol extraction solution. After stirring, the activated carbon is removed. Water and alcohol are removed from the remaining solution. The resulting substance is different from known water-soluble anti-oxidation agents, which absorb strongly in the ultraviolet range indicative of the presence of one or more aromatic rings ($\lambda_{max}$=250–300 nm). Surprisingly, the substances obtained with the method of the present invention have ultraviolet absorption spectra that show little or no absorption of light between 250 and 300 nm. The compounds of the present invention also exhibit anti-oxidation properties which are superior to those of known water-soluble anti-oxidation agents.

The seasoning herbs which may be used in the present invention include rosemary, sage, mace, thyme, oregano, nutmeg, ginger, cinnamon, clove, basil, marjoram, mustard, savory, laurel, anise, and the like, but the invention is not limited to these. Furthermore, the herbs may be in their original state, or crushed or pulverized forms may be used.

The carbon dioxide used in the present invention is normally used in a liquid form, but can also be used as a gas in subcritical or supercritical conditions. In the case of subcritical or supercritical conditions, temperature, pressure, and the like can be chosen as appropriate for the processing requirements. For example, when the herbs are processed by carbon dioxide liquid, the pressure is about 30 to about 70 kg/cm$^2$, and the temperature is about 0° C. to about 25° C. When using critical state carbon dioxide gas, the pressure is about 71 kg/cm$^2$ or greater, and the temperature is about 0° C. to about 30° C. When using supercritical condition carbon dioxide gas, the pressure is about 75 kg/cm$^2$ or greater, and the temperature is about 32° C. or greater.

Organic solvents can be used in place of, or with, carbon dioxide liquid to remove oil soluble portions of the seasoning herbs. When the oil removal process is performed using carbon dioxide liquid and an organic solvent, it may be performed either sequentially, or it may be done simultaneously. Examples of appropriate organic solvents include ethyl acetate, methanol, chloroform, dichloroethane, ethyl ether, and the like. These organic solvents can be used at between about 0.2–50 times by weight with respect to the raw material of seasoning herbs, and preferably at about 2–5 times by weight. Generally, by reacting at about 5° C. to 60° C. for between about 1 to 48 hours, oil-soluble portions of the seasoning herbs are substantially or completely removed. After removal of the oil-soluble fraction, the remaining oil-insoluble portion is further processed. In this step, 0.2–50 times by weight, and preferably about 2–10 times by weight, of 40–60% hydrated alcohol, such as methanol or ethanol, is added to the resulting oil-insoluble portion. By removing the solvent from the resulting hydrated alcohol extraction solution by well-known techniques, it is possible to obtain the water-soluble anti-oxidation agent of the present invention. Depending on the degree of coloration of the hydrated water alcohol extraction solution as described above, activated carbon may be added and stirred as required. Afterward, the activated carbon may be removed by filtering the solution, and the solvent can be removed by techniques well-known in the art.

The water-soluble anti-oxidation agents obtained by the present invention are clearly different from known water soluble anti-oxidation agents, as analyzed by ultraviolet spectroscopy. The compounds of the present invention absorb minimally in the ultraviolet range, and only at the end of the absorption spectrum ($\lambda_{max}$=220 nm or less). The anti-oxidation effects of the compounds of the present invention are also superior to known water-soluble anti-oxidation agents.

The water-soluble antioxidant of the present invention can be used in a wide number of products including fruit juices; processed meat foods, such as ham, sausage, and the like; foods which contain water, such as processed aquatic foods and the like; oil-based foods, such as butter, margarine, mayonnaise, salad dressing, and the like; scented toiletries, such as soap, shampoo, detergent, lotion, foundation, aromatic agents, hair styling material, and the like; and natural essential oils, such as lemon oil, lime oil, grapefruit oil, orange oil, and the like.

Embodiment 1

Dried rosemary leaves (1 kg) were processed with liquid carbon dioxide gas for 2 hours at 20° C. and 50 kg/cm$^2$ of pressure. After processing, 50% hydrated ethanol (500 ml) was added to the oil-insoluble residue. After stirring for 1 hour, the extract was filtered. Activated carbon (600 g) was added to the filtrate, and the suspension was stirred. After removal of the activated carbon and the solvent, 14 g of water-soluble anti-oxidation agent was obtained.

The molecular weight of the water-soluble anti-oxidation agent was determined by gel permeation to be between 200–4,000. IR absorption was measured, using a FT-IR-5300 spectrometer (JASCO, Japan). Ultraviolet absorption spectra were measured, using a DU64 UV spectrophotometer (Beckman Instruments, USA). NMR spectra were obtained with a GSX-500 spectrometer (JEOL, USA). The data obtained was as follows:

IR: 3,600–2,800 (OH); 1,610; 1,400; 1,100
UV absorption spectra: $\lambda_{max}$<220 nm
NMR: 0.8–1.2 (m), 1.6–1.8 (m), 4.0–4.2 (m), 4.4 (m), 5.1 (m), 5.4 (m), 8.25 (non aromatic)

Embodiment 2

Clary sage roots (6 kg) were crushed and processed in 14 l of a solvent mixture of ethyl acetate and methanol (volume ratio 1:1). After processing, solvent separation with water and ethyl acetate (volume ratio 1:1) was conducted on the residual extracted product. Afterwards, 1000 ml of 50% hydrated ethanol was added to the extracted solution. After stirring for 1 hour, the solution was filtered. Activated carbon (3.8 kg) was added to the obtained filtrate, and the solution was stirred. After removal of the activated carbon and the solvent, 84 g of water soluble anti-oxidation agent was obtained.

The physical chemical properties of this substance were as the following:

Molecular weight: 200–4,000 (gel permeation chromatography)
IR: 3,350 (OH); 2,925; 2,850; 1,590; 1,420; 1,050
UV absorption spectra: $\lambda_{max}$<220 nm
NMR: 0.9 (m), 1.2 (m), 1.7 (s), 2.05 (s), 2.2 (s), 3.0–4.2 (m), 4.4 (m), 4.45 (m), 5.1 (m), 5.4 (m), 8.25 (non aromatic)

The ultraviolet absorption spectra of Embodiment 1 and Embodiment 2 are shown in FIG. 1, and compared with the absorption spectrum of the water-soluble anti-oxidation compound of Japanese Examined Patent Number 58-37,351. It can be seen that the absorption spectra of the compounds of the present invention differ dramatically from that of the prior art water-soluble compound. The compounds of Embodiment 1 and Embodiment 2 absorb UV light at a significant level only below 220 nm, and virtually none at all above 240 nm. The water-soluble anti-oxidation compound of Japanese Examined Patent Number 58-37,351, in contrast, has absorption maxima near 285 nm and 330 nm, and also absorbs UV light significantly above 220 nm.

TEST EXAMPLE 1

Anti-oxidation activity

Figure 2:
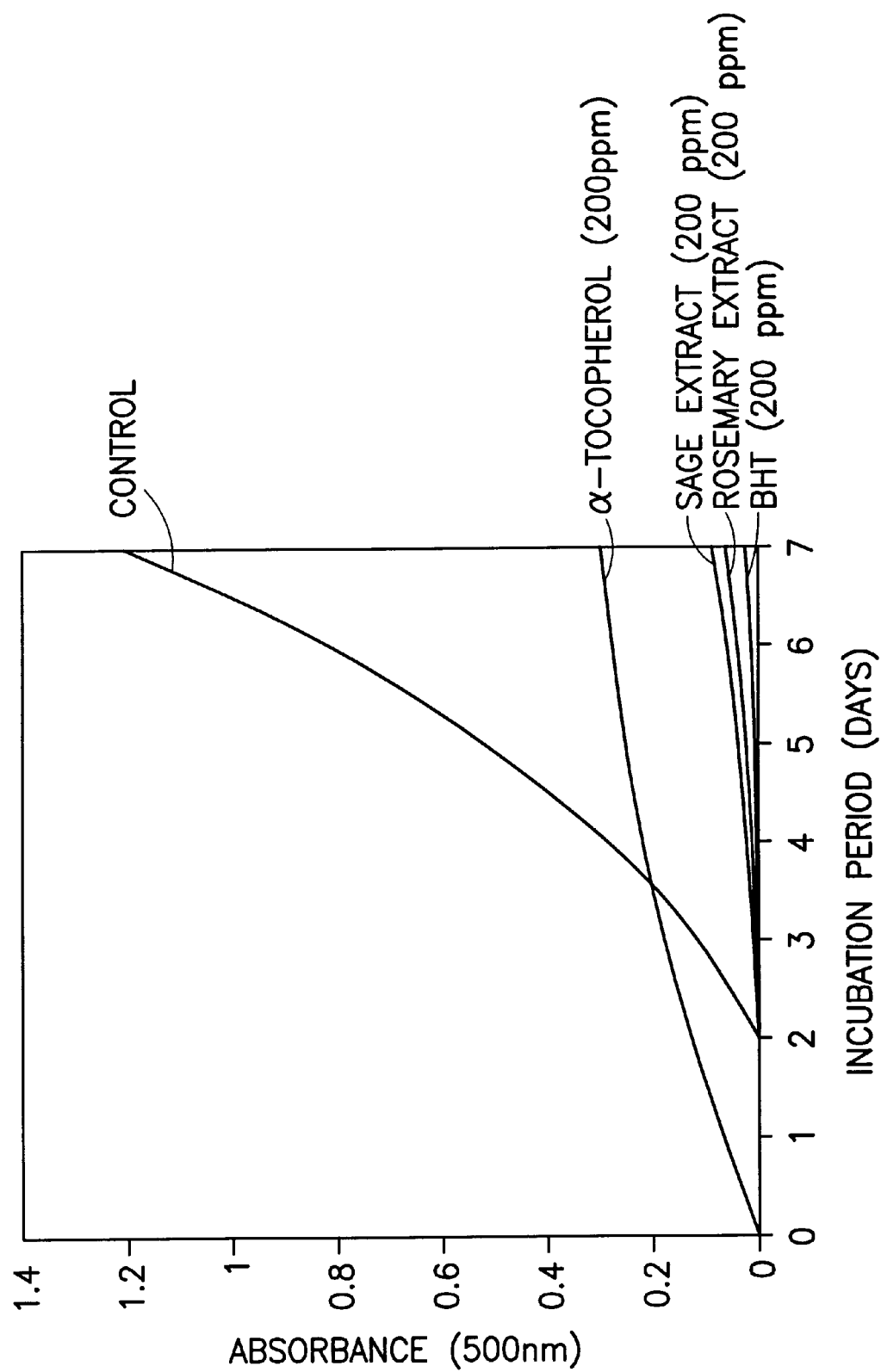
FIG. 2 is a graph showing the anti-oxidative activity of the compounds of the present invention.

Antioxidation activity was tested by the Rodin iron method. Samples were prepared in a water/ethanol solution (pH 7) containing linoleic acid (0.52%). Each sample contained 0.02% by weight of one of the substances obtained from Embodiment 1 or Embodiment 2. Positive controls contained 0.02% of BHT or alpha-tocopherol, and a negative control contained no addition. The samples were incubated in a 50° C. constant water bath for 7 days. Thereafter, each of the sample solutions were measured for absorbance at 500 nm. The results are shown in FIG. 2.

Both of the water soluble anti-oxidation products obtained through the present invention showed an equivalent or superior anti-oxidation strength to the negative control (linoleic acid) and the positive controls (alpha-tocopherol and BHT).

USAGE EXAMPLE 1

Application in a cosmetic product

Figure 3:
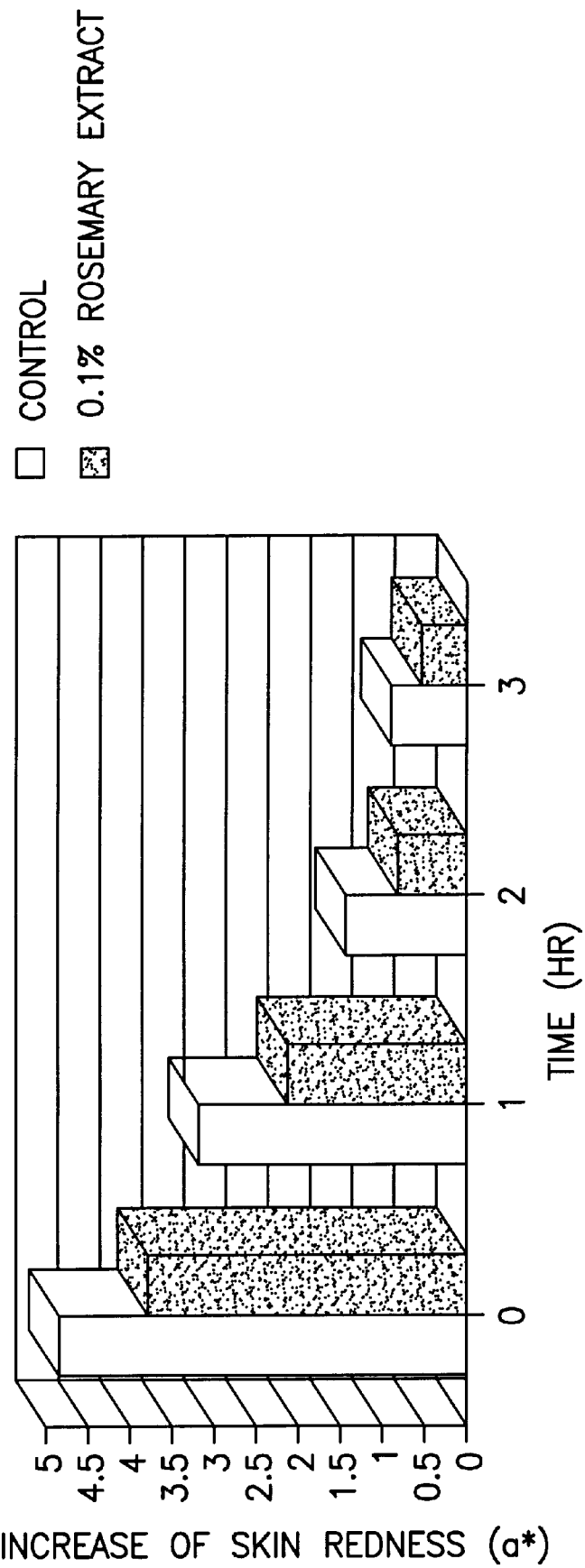
FIG. 3 is a graph showing the anti-irritation activity of the compounds of the present invention.

The compound of Embodiment 1 was tested for topical anti-irritation activity. A 40×40 mm test area was outlined on both volar forearms of 5 human volunteers. A lotion containing 0.1% of the test compound of Embodiment 1 was prepared, and 30 μl of the lotion was applied onto the test areas twice a day for 3 consecutive days. As a control, the lotion solution lacking the test compound was applied. On the fourth day, an aqueous solution of methyl nicotinate (an irritant) was applied in the test areas, and the redness of the skin measured using a Minolta CM-508d spectrophotometer. The results are shown in FIG. 3. It can be seen that addition of the test compound of Embodiment 1 to the forearms of the volunteers diminished the irritation produced by the methyl nicotinate.

USAGE EXAMPLE 2

Application in a beverage product

Figure 4:
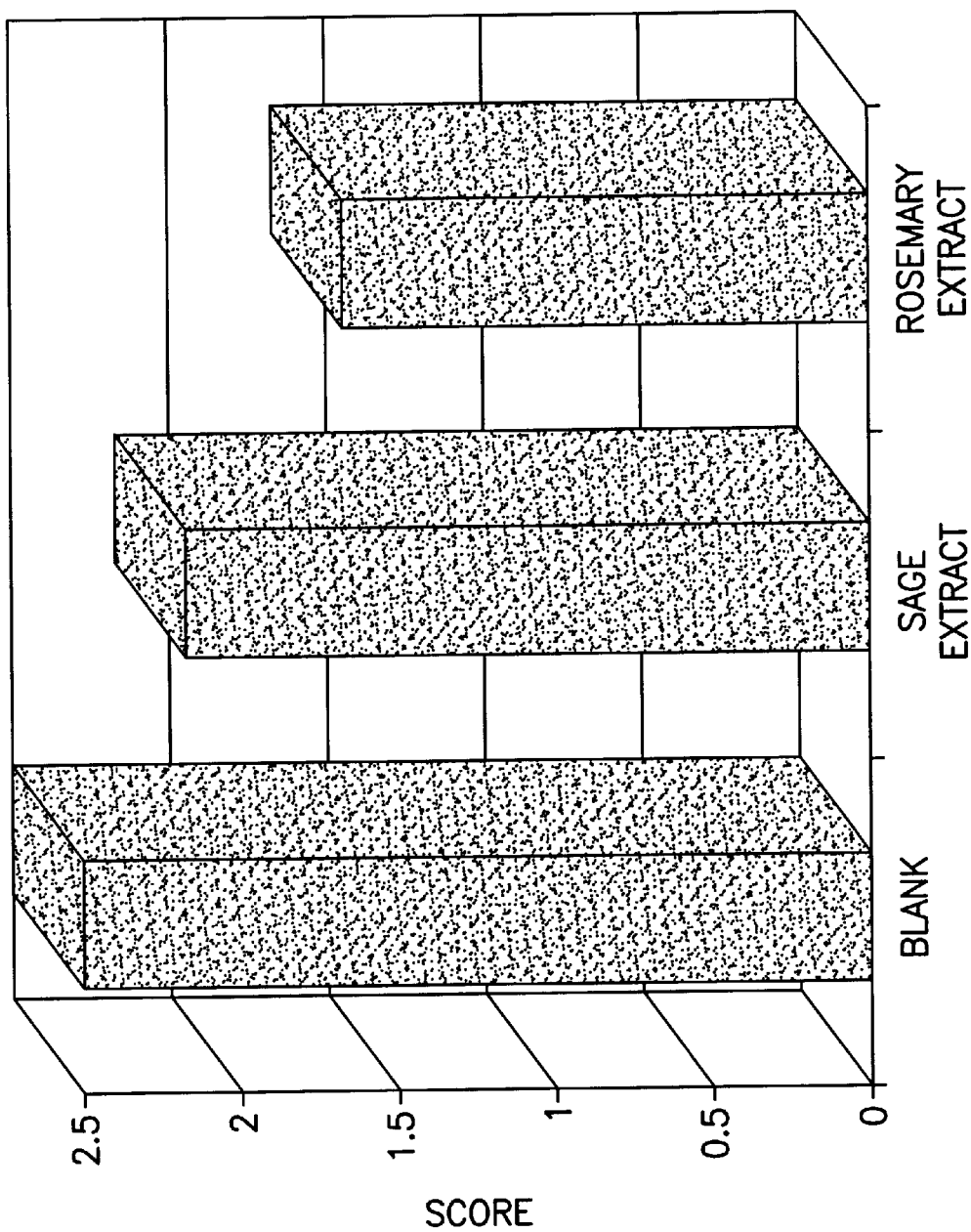
FIG. 4 is a graph of anti-deterioration of the compounds of the present invention.

The compounds of Embodiment 1 and Embodiment 2 were tested for their abilities to protect lemon beverages against oxidative deterioration. The beverages were stored in an incubator at 37° C. for five days. The test samples contained 0.02% of the compounds of Embodiment 1 or Embodiment 2. One negative control contained no addition. Six panelists tasted the samples and compared each to a fresh lemon beverage sample. The samples were rated on a scale between 0 and 6, with 0 being no change and 6 being excessively damaged. The results are shown in FIG. 4. Both compounds of the present invention inhibited deterioration when included in the lemon beverage samples, compared to the negative control lacking any addition.

Having described preferred embodiments of the invention, it is to be understood that the invention is not limited to those precise embodiments, and that various changes and modifications may be effected therein by one skilled in the art without departing from the scope or spirit of the invention as defined in the appended claims.

What is claimed is:

1. A method for producing a water-soluble anti-oxidation agent, comprising the steps of:

processing at least one of rosemary and sage to remove fats and oils, such that an oil-insoluble residue portion is produced;

contacting said oil-insoluble residue portion with hydrated alcohol to produce a mixture; and removing water and alcohol from said mixture, whereby said water-soluble anti-oxidation agent is produced.

2. A water soluble anti-oxidation agent produced by the method of claim 1.

* * * * *